United States Patent [19]

van Geem et al.

[11] Patent Number: 4,927,974

[45] Date of Patent: May 22, 1990

[54] PROCESS FOR THE PREPARATION OF CYCLOHEXANOL AND/OR CYCLOHEXANONE

[75] Inventors: Paul C. van Geem, Beek; Franciscus T. B. van den Brink, Geldrop, both of Netherlands

[73] Assignee: Stamicarbon B.V., AC Geleen, Netherlands

[21] Appl. No.: 334,142

[22] Filed: Apr. 6, 1989

[30] Foreign Application Priority Data

Apr. 21, 1988 [NL] Netherlands ................ 8801036

[51] Int. Cl.$^5$ ............................................. C07C 45/32
[52] U.S. Cl. ................................. 568/357; 568/835; 568/360; 568/836
[58] Field of Search ............... 568/357, 835, 356, 836, 568/360, 830

[56] References Cited

U.S. PATENT DOCUMENTS

| | | | |
|---|---|---|---|
| 4,339,604 | 7/1982 | van Geem et al. | 568/357 |
| 4,507,512 | 3/1985 | Okumura et al. | 568/835 |
| 4,528,409 | 7/1985 | Mitsui et al. | 568/835 |
| 4,588,846 | 5/1986 | Mitsui et al. | 568/835 |

FOREIGN PATENT DOCUMENTS 53847 6/1982 European Pat. Off. ............ 568/835

OTHER PUBLICATIONS

Don et al., Chem. Abst., vol. 97, #181822r (1982).

*Primary Examiner*—James H. Reamer
*Attorney, Agent, or Firm*—Cushman, Darby & Cushman

[57] ABSTRACT

The invention relates to a process for preparing cyclohexanol and/or cyclohexanone, in which cyclohexene in a feed stream containing cyclohexene, cyclohexane and benzene is hydrated into cyclohexanol and/or oxidized into cyclohexanone, the cyclohexanol and/or cyclohexanone formed is separated from the reaction mixture thus obtained and the remaining cyclohexane and benzene are recycled to a preconnected cyclohexene preparation section, part of the stream that is recycled to the cyclohexene preparation section being subjected to a dehydrogenation reaction and the remaining part to a hydrogenation reaction, and the reaction streams thus obtained being combined to form the feed stream to the hydration and/or oxidation step.

5 Claims, 1 Drawing Sheet

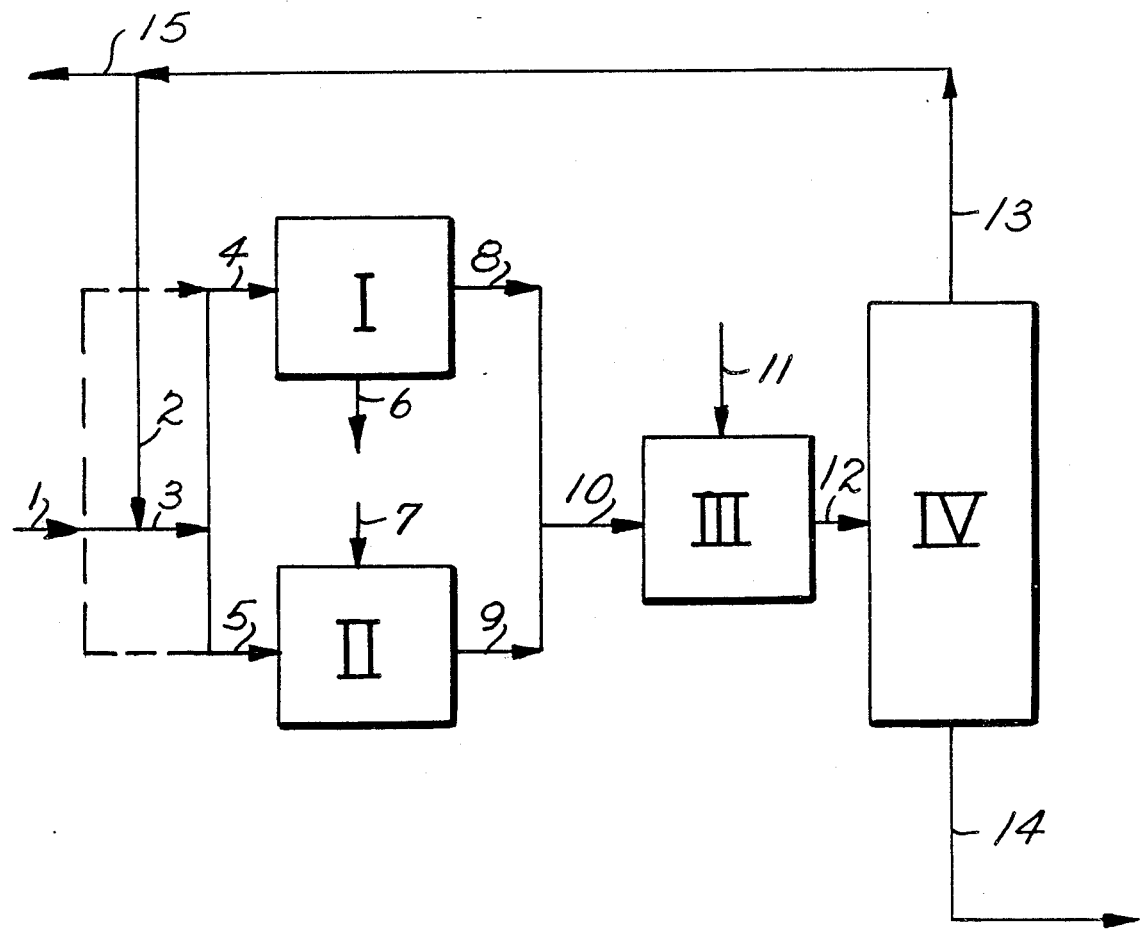

PROCESS FOR THE PREPARATION OF CYCLOHEXANOL AND/OR CYCLOHEXANONE

The invention relates to a process for the preparation of cyclohexanol and/or cyclohexanone, in which cyclohexane in a feed stream containing cyclohexene, cyclohexane and benzene is hydrated to cyclohexanol and/or oxidized to cyclohexanone, the cyclohexanol and/or cyclohexanone formed is separated from the reaction mixture thus obtained and the remaining cyclohexane and benzene are recycled to a preconnected cyclohexene preparation section.

Such a process is described in US-A-4.339.604, in which by a hydrogenation reaction benzene is converted into a mixture of cyclohexene, unconverted benzene and cyclohexane as a side product. The stream recycled to the cyclohexene preparation section is first subjected to a dehydrogenation reaction to convert all of the cyclohexane (and any cyclohexene) present in this stream into benzene, which can then be used along with fresh benzene in the hydrogenation reaction.

An alternative process for preparing cyclohexanol and/or cyclohexanone from cyclohexene is described in EP-A-53.847, in which, via dehydrogenation of cyclohexane, a cyclohexene-containing feed stream is obtained which is then subjected to a hydration or oxidation reaction, and in which the return stream is subjected to a hydrogenation to convert all of the benzene (and any cyclohexene) present in this stream into cyclohexane, which can then once again be used along with fresh cyclohexane in the dehydrogenation reaction.

However, the processes described above present a number of disadvantages. The choice of the process depends greatly on the availability of the raw material (cyclohexane or benzene), which dependence is increased by the fact that in the dehydrogenation or hydrogenation of the return stream the conversion into the raw material (benzene or cyclohexane, respectively) must be as complete as possible because otherwise an accumulation of cyclohexane or benzene, respectively, in the process will result. In addition, the selectivity of the conversion into cyclohexene determines the size of the process streams, in particular the size of the return stream and the volume to which the complete dehydrogenation or hydrogenation of the return stream must be accomplished.

Alternatives, notably the separation of cyclohexene, cyclohexane or benzene from a feed stream, have often been described. US-A-4.339.604, for example, describes how cyclohexane can be separated from benzene and/or cyclohexene by means of an extractive distillation. EP-A-248.422 describes an azeotropic distillation in which the cyclohexene is separated from cyclohexane and benzene. These types of separation are difficult and hence expensive.

The process according to the invention does not require such an expensive separation of reaction products and the other aforementioned disadvantages are also avoided. The process is characterized in that part of the stream that is recycled to the cyclohexene preparation section is subjected to a dehydrogenation reaction and the remaining part to a hydrogenation reaction and the reaction streams thus obtained are combined to form the feed stream to the hydration and/or oxidation step (the so-called oxygenation step). In said dehydrogenation reaction, cyclohexane is converted to cyclohexene; in said hydrogenation reaction, benzene is converted to cyclohexene.

As raw material for the process according to the invention benzene, cyclohexane and also mixtures of these two components may be used. Because of this, the process is less dependent on the raw material. This raw material may then be supplied to the dehydrogenation step, the hydrogenation step and/or the return stream to the cyclohexene preparation section, according to the type of raw material used.

Because the cyclohexene is obtained by hydrogenation (of benzene) as well as by dehydrogenation (of cyclohexane) in the process according to the invention, it is no longer necessary to have the return stream completely converted into the raw material before preparing the cyclohexene. Better still: the conditions of the hydrogenation step can be chosen so that optimum conversion is obtained of the benzene present in the feed stream into cyclohexene; the conditions of the dehydrogenation step can be chosen so that optimum conversion is obtained of the cyclohexane present in the supply stream into cyclohexene. In both of these process steps more favourable conditions can therefore be applied than in the state of the art processes and thus the overall reaction requires less $H_2$ handling (for there is no longer any need for an extensive dehydrogenation or hydrogenation of the return stream). It has been found that the presence of cyclohexane in the hydrogenation step and the presence of benzene in the dehydrogenation step do not adversely affect the formation of cyclohexene in those reactions. The process according to the invention permits a higher degree of conversion of the raw material because the cyclohexane and benzene side products formed can be used directly as raw materials for the process according to the invention via the return stream. Preferably, the hydrogen released in the dehydrogenation step is used for the hydrogenation reaction.

The dehydrogenation of cyclohexane to cyclohexene can be effected in any known manner. A suitable manner as described in, for example, Kinetics and Catalysis, Vol. 20 (2), pp. 323-327 (1979), to which, for the sake of brevity, the reader is referred. According to the known method, cyclohexene is prepared by an oxidative dehydrogenation of cyclohexane by passing cyclohexane and air over a zeolitic catalyst at 200°-650° C. (preferably 300°-600° C.), at a pressure of 0.001-1 MPa (preferably 0.01-0.5 MPa). The oxygen/cyclohexane molar ratio is preferably between 1:2 and 3:2.

The hydrogenation of benzene into cyclohexene may, for example, be effected in the gas phase, with a catalyst containing an element of group VI or group VIII of the periodic table of elements, such as ruthenium, palladium, nickel, or platinum. Suitable catalysts are, for instance, platinum/aluminium oxide or a palladium-nickel alloy. The reaction temperature is, for example, 150°-400° C., the pressure is, for instance, 0.01-5 MPa, and is preferably higher than 0,2 MPa. For the sake of brevity, the reader is referred to EP-B-55.495 for a suitable embodiment of this part of the process. The hydrogenation can also be effected in the liquid phase, with a catalyst, for example with a suspension catalyst such as ruthenium black or with ruthenium applied to a carrier. The reaction temperature is, for example, 25°-300° C., and the pressure is, for instance, 0.3-1 MPa, although higher and lower pressures are also suitable, but economically unfavourable. For the sake of brevity, the reader is referred to US-A-4.665.274 for a suitable embodiment of this part of the process.

The benzene/cyclohexane molar ratio in the return stream is preferably between 5:1 and 1:5 so that the optimum conditions for the highest possible yield of cyclohexene can be obtained in the dehydrogenation step as well as in the hydrogenation reaction.

The ratio in which the return stream is divided between the two reaction steps depends on a number of factors. In the first place it is determined by the type of raw material used (cyclohexane or benzene or a mixture of the two); in addition, it depends on the activity and the selectivity of the catalytic systems used in the two process steps. Preferably, the stream is divided on the basis of the cyclohexane/benzene ratio in the feed stream to the cyclohexanol/cyclohexanone preparation section.

The cyclohexene-containing feed stream obtained according to the process of the invention can be converted into cyclohexanol and/or cyclohexanone via an oxygenation step according to methods known in the art.

For example, the cyclohexene can be converted into cyclohexene oxide by means of a reaction with sodium hypochlorite and subsequent saponification, followed by isomerisation of the cyclohexene oxide into cyclohexanone. Such an isomerisation is described in EP-A-192.298.

Another suitable method for oxidizing the cyclohexene is the Wacker oxidation reaction, which yields the desired cyclohexanone in one reaction step; a very suitable process for this reaction is described in EP-A-210.705 in which a vanadium and a palladium component, applied to a carrier, the surface of which is covered with hydroxyl groups, is used as catalyst. The vanadium is present in the form of a surface vanadate. γ-alumina proved to be a very suitable carrier material; further research showed that $TiO_2$, in the anatase form, is also a very good carrier material.

The cyclohexane can also be converted, via a hydration reaction, into cyclohexanol. This hydration of cyclohexene to cyclohexanol can be carried out in any known manner. Usually an acid catalyst is used. Very suitable methods are described in the British patents 1.381.149 and 1.542.996, to which reference is made for the sake of brevity. Sulphuric acid is a very suitable catalyst. Iron(III) sulphate may be used as co-catalyst. The hydration is usually carried out as a process with separate steps consisting of (1) the addition of the acid to the double bond of the cyclohexene with the formation of the ester of cyclohexanol and the acid, e.g. cyclohexyl hydrogen sulphate and (2) hydrolysis of the cyclohexyl ester to form cyclohexanol and the acid. The first step may be effected at a temperature of, for example, $-50°$ C. to $+30°$ C., but temperatures of $30°-100°$ C. are also possible, and the second step at $50°-150°$ C. The hydration of the cyclohexene can also be effected with other catalysts, for example with a strongly acid ion exchanger, e.g. a crosslinked polystyrene resin containing sulphonic acid groups or with a crystalline aluminium silicate, if so desired in the presence of an acid. The latter process is described in, for instance, US-A-4.661.639.

The feed stream containing cyclohexene may also be pretreated before being fed to the oxygenation step to increase the cyclohexene concentration. To this end, use may be made of, for example, the process described in EP-A-248.422. This concentration presents the advantage that the streams that are to be processed in the subsequent process steps, that is, the oxygenation and the separation of the cyclohexanol and/or cyclohexanone from the reaction mixture thus obtained, will be smaller. The complete or partial removal of components that are inert with respect to these process steps (mainly benzene and cyclohexane) greatly reduces the size of the feed stream to the oxygenation step and therefore the equipment required for the aforementioned process steps may be proportionately smaller. The stream that is also released in this concentration step (containing mainly benzene and cyclohexane, in addition to a little cyclohexene) can be supplied to the cyclohexene preparation section according to the process of the invention.

The oxidation of hydration of the cyclohexene can be effected in the presence of the cyclohexane and/or the benzene.

After the aqueous phase has been removed from the reaction mixture of the hydration and/or oxidation step, an organic phase remains, which, in addition to the cyclohexanol and/or cyclohexanone formed, contains benzene, cyclohexane and any unconverted cyclohexene. Cyclohexanol and/or cyclohexanone is separated from this mixture, for example by distillation, after which a fraction consisting of benzene, cyclohexane and any cyclohexene is obtained that boils at a lower temperature than cyclohexanol and/or cyclohexanone.

With the process according to the invention it is not necessary to laboriously separate this last fraction into its components, or to completely convert it into cyclohexane or benzene. On the contrary, it can be fed in its entirety directly to the cyclohexene preparation section; accumulation of undesired side-products, such as methylcyclopentane, can be prevented with the aid of a purge.

Pure cyclohexanol can be obtained from the crude cyclohexanol obtained by means of distillation. If so desired, the cyclohexanol can be dehydrogenated to cyclohexanone in a manner known in the art. The hydrogen obtained in such a dehydrogenation can be used as a hydrogen-feed to the hydrogenation step of the claimed process. Pure cyclohexanone can be obtained, once again via distillation, from the crude cyclohexanone obtained in the oxidation or in the dehydrogenation of cyclohexanol, which pure cyclohexanone is very suitable as a raw material for caprolactam preparation.

The invention is further elucidated with the aid of the included figure, without limiting the scope of the invention. This figures shows a simplified diagram of the process.

The fresh raw material (cyclohexane, benzene or a mixture hereof) is combined with return stream (2) via line (1), after which the stream (3) thus obtained is split up into a stream (4), which is fed to the dehydrogenation reactor I, and a stream (5), which is fed to the hydrogenation reactor II. Preferably, part or all of the hydrogen stream (6) leaving the dehydrogenation reactor I is used as hydrogen feed (7) to the hydrogenation reactor II. The reaction stream (8) leaving the dehydrogenation reactor is fed as feed (10) to the cyclohexanol/cyclohexanone reactor III together with the reaction stream (9) leaving the hydrogenation reactor. Stream (3) is split up into (4) and (5) on the basis of the benzene/cyclohexane ratio in (10). A water-containing feed (for the hydration into cyclohexanol) and/or an O2-component-containing feed (for the oxidation into cyclohexanone) is fed to reactor III via stream (11). After conversion in III, reaction stream (12) is separated, if necessary, into an organic layer containing cyclohexanol and/or cyclohexanone and an aqueous layer, in a separator not shown in the figure. The organic layer is fed to the distillation column IV. In this column the benzene, cyclohexane, any cyclohexene and other low-boiling components present in (12) are separated (stream (13)) from the crude cyclohexanol and/or cyclohexanone (stream (14)). The crude cyclohexanole and/or cyclohexanone can be worked up into pure cyclohexanol, or into pure cyclohexanone via an additional dehydrogenation step. Stream (13) is recycled to the cyclohexene preparation section (reactors I and II) after a purge stream (15) has been diverted from it.

The invention will be elucidated by the following, non restrictive examples. Reference is given to the figure.

EXAMPLE I

To the dehydrogenation reactor I, filled with a 50 ml Na, K-erionite zeolite, one feeds a stream of 196 grams/hour, consisting of 66 wt% benzene, 32.6 wt.% cyclohexane and 1.4 wt.% cyclohexene which, at a temperature of 400° C. and a pressure of 1 MPa, is converted to cyclohexene with a yield of 54%.

To the hydrogenation reactor II, a 1 liter autoclave filled with a Ru-catalyst made according to example 1 of EP-A-220.525, a same mixture, in an amount of 173 grams/hour is fed, which, at a temperature of 160° C. and a pressure of 8 MPa, is converted to cyclohexene with a yield of 48%.

The so obtained process streams 8 and 9 are combined as a feedstream (10) to the oxygenation reactor III, said stream consisting of 41,6% benzene, 25,8% cyclohexene and 32,6% cyclohexane. Stream 10 is converted in III via a Wacker-oxidation process, using a $PdCl_4/CuCl_2$ catalyst, at a temperature of 90° C. and a pressure of 0.3 MPa with a yield of 95%. After separation in IV, 112 grams/hour of cyclohexanone are obtained. The recyclestream 2, being 99% of stream 13, is mixed up with 90 grams/hour of fresh benzene (stream 1) and, according to the above indicated split, divided over reactors I and II.

EXAMPLE 2

Example I is repeated, but instead of benzene, one uses a fresh feed of 110 grams/hour of cyclohexane (stream 1). To reactor I a stream of 205 grams/hour, consisting of 6.8 wt% benzene; 1.2 wt.% cyclohexene and 92% cyclohexane, to reactor II a same mixture, in an amount of 181 grams/hour are fed. After separation in IV, 127 grams/hour of cyclohexanone are obtained.

EXAMPLE III

Example I is repeated, but the fresh feed (1) consists of a mixture of benzene and cyclohexane (100 grams/hour; 48.1 wt.% benzene). To reactor I a stream of 201 grams/hour, (consisting of 37.8 wt.% benzene; 1.5 wt.% cyclohexene and 60.7 wt.% cyclohexane), to reactor II a same mixture, in an amount of 179 grams/hour are fed. After separation in IV, 117 grams/hour of cyclohexanone are obtained.

EXAMPLE IV

Example I is repeated, but in reactor III the cyclohexene is converted via a hydration reaction, using a strong acid ion exchange resin as a catalyst, at a temperature of 90° C. and a pressure of 0.3 MPa, said hydration-reaction having a yield of 20%.

The fresh feed (41.4 grams/hour of benzene), in combination with the recycle stream 2, are send to reactors I and II in amounts of 174.5 and 155 grams/hour, respectively (the flows consisting of 34.2 wt.% benzene, 48.8 wt.% cyclohexene and 17.0 wt.% of cyclohexane). A cyclohexanol-stream of 49.5 grams/hour is obtained.

We claim:

1. Process for the preparation of cyclohexanol and/or cyclohexanone, in which cyclohexene in a feed stream containing cyclohexene, cyclohexane and benzene is hydrated into cyclohexanol and/or oxidized into cyclohexanone, the cyclohexanol and/or cyclohexanone obtained is separated from the reaction mixture thus obtained and the remaining cyclohexane and benzene are recycled to a preconnected cyclohexene preparation section, wherein part of the stream that is recycled to the cyclohexene preparation section is subjected to a dehydrogenation reaction and the remaining part to a hydrogenation reaction and the reaction streams thus obtained are combined to form the feed stream to the hydration and/or oxidation step.

2. Process according to claim 1, characterized in that part or all of the hydrogen obtained in the dehydrogenation step is used in the hydrogenation step.

3. Process according to claim 1, characterized in that the benzene and cyclohexane in the recycled stream are in a molar ratio of 5:1-1:5.

4. Process according to claim 1, characterized in that the ratio in which the recycled stream is divided between the hydrogenation section and the dehydrogenation section is based on the benzene/cyclohexane ratio in the feed stream.

5. Process according to claim 1, characterized in that the feed stream is pretreated to increase the cyclohexene concentration and the stream thus treated is fed to the hydration and/or oxidation step.

* * * * *